(12) United States Patent
Foster et al.

(10) Patent No.: US 9,155,734 B2
(45) Date of Patent: *Oct. 13, 2015

(54) STABILITY OF HYDROMORPHONE HYDROCHLORIDE SOLUTIONS

(71) Applicant: Mallinckrodt LLC, Hazelwood, MO (US)

(72) Inventors: John J. Foster, St. Paul, MN (US); Thomas R. Prentice, St. Paul, MN (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/787,042

(22) Filed: Mar. 6, 2013

(65) Prior Publication Data
US 2013/0237558 A1    Sep. 12, 2013

Related U.S. Application Data

(60) Provisional application No. 61/607,774, filed on Mar. 7, 2012.

(51) Int. Cl.
| A61K 31/485 | (2006.01) |
| A61K 9/00 | (2006.01) |
| A61K 9/08 | (2006.01) |

(52) U.S. Cl.
CPC .............. *A61K 31/485* (2013.01); *A61K 9/0019* (2013.01); *A61K 9/0085* (2013.01); *A61K 9/08* (2013.01)

(58) Field of Classification Search
USPC ........................................................ 514/282
See application file for complete search history.

(56) References Cited

U.S. PATENT DOCUMENTS

| 6,589,960 B2 | 7/2003 | Harclerode et al. |
| 8,188,048 B2 | 5/2012 | Lewis |
| 8,268,774 B2 | 9/2012 | Ellis et al. |
| 8,410,129 B2 | 4/2013 | Brooks-Korn |
| 8,461,171 B2 | 6/2013 | Holaday et al. |
| 2003/0045720 A1 | 3/2003 | Harclerode et al. |
| 2004/0102476 A1 | 5/2004 | Chan et al. |
| 2010/0216842 A1 | 8/2010 | Nabeta et al. |
| 2012/0270848 A1 | 10/2012 | Mannion et al. |
| 2012/0310140 A1 | 12/2012 | Kramer et al. |
| 2013/0041241 A1 | 2/2013 | Felts et al. |
| 2013/0096066 A1 | 4/2013 | Ellis et al. |

FOREIGN PATENT DOCUMENTS

| EP | 2446882 | 5/2012 |
| WO | 9711681 | 4/1997 |
| WO | 2012075337 A2 | 6/2012 |
| WO | 2013063263 A1 | 5/2013 |
| WO | 2013071138 A1 | 5/2013 |

OTHER PUBLICATIONS

Hildenbrand et al. Stability and Compatibility of Hydromorphone Hydrochloride in an Implantable Infusion System. J. of Pain and Symptom Management. 2001, vol. 22, pp. 1042-1047.*
Purdue Pharma, L.P., Full Prescribing Information. Oct. 2011 (hhtp://app.purduepharma.com/xmlpublishing/pi.aspx?id=di).*
Dilaudid-HP Injection Package Insert.
Boswell et al, "Interventional Techniques: Evidence-based Practice Guidelines in the Management of Chronic Spinal Pain"; Pain Physician 2007; 10:7-111.
Deer et al, "Polyanalgesic Consensus Conference 2007: Recommendations for the Management of Pain by Intrathecal (Intraspinal) Drug Delivery: Report of an Interdisciplinary Expert panel"; Neuromodulation: Technology at the Neural Interface; Intl Neuromodulation Society; vol. 10; No. 4, 2007pp. 300-328.
Anderson et al. "Intrathecal Hydromorphone for Chronic Nonmalignant Pain: A Retrospective Study"; American Academy of Pain Medicine; vol. 2; No. 4, 2001; pp. 287-297.
Allen et al.; "Opiate Pharmacology of Intrathecal Granulomas"; the American Society of Anesthesiology 2006; 105: 590-8.
Smith et al., "Intrathecal Drug Delivery"; Pain Physician Journal 2008; Opioid Special Issue; 11; S89-S104.
Roy et al, "Solubility and Related Physicochemical Properties of Narcotic Analgesics"; Pharmaceutical Research, vol. 5, No. 9, 1988; 580-586.
Ramsey et al., "Intrathecal Granuloma in a Patient Receiving High Dose Hydromorphone"; Pain Physician Journal; 2008; 11:3:369-373.
Johansen et al.; "Continuous Intrathecal Infusion of Hydromorphone: Safety in the Sheep Model and Clinical Implications"; American Academy of Pain Medicine; vol. 5; No. 1; 2004; pp. 14-25.
Du Pen et al.; "Intrathecal Hydromorphone for Intractable Nonmalignant Pain: A Retrospective Study"; American Academy of Pain Medicine; vol. 7; No. 1; 2006; pp. 10-15.
Ahern, et al., "Safety and Efficacy of Low-dose Ketamine Added to a Hydromorphone Titration Protocol for Emergency Department Patients With Acute Severe Pain," Annals of Emergency Medicine, 2012, vol. 60, No. 4S, p. S53, Abstract No. 146.
Gagnon, et al., "Tremors and Agitation Following Low-Dose Intravenous Hydromorphone Administration in a Patient with Kidney Dysfunction," Annals of Pharmacotherapy, 2013, vol. 47, pp. e34.
Oldenmenger, et al., "Efficacy of opioid rotation to continuous parenteral hydromorphone in advanced cancer patients failing on other opioids," Support. Care Cancer, 2012, vol. 20, pp. 1639-1647.
Chang, et al., "Randomized Clinical Trial of an Intravenous Hydromorphone Titration Protocol versus Usual Care for Management of Acute Pain in Older Emergency Department Patients," Drugs Aging, published online on Jul. 12, 2013, DOI 10.1007/s40266-013-0103-y.
Guzman, et al., "Evaluation of thermal antinociceptive effects after intramuscular administration of hydromorphone hydrochloride to American kestrels (*Falco sparverius*)," Am. J. Vet. Res., 2013, vol. 74, pp. 817-822.

(Continued)

*Primary Examiner* — Melenie McCormick
*Assistant Examiner* — Taina D Matos Negron

(57) ABSTRACT

The present invention relates generally to a sterile hydromorphone hydrochloride solution that is substantially free of buffer.

8 Claims, No Drawings

(56) References Cited

OTHER PUBLICATIONS

Sun, et al., "Determination of hydromorphone in human plasma by a sensitive RP-HPLC-ESI-MS method and its application to a clinical pharmacokinetic study in postoperative patients after low dose intravenous administration with infusion pump," J. Pharm. Biomed. Anal., 2012, vol. 61, pp. 15-21.

Chang, et al., "Randomized Clinical Trial of the 2 mg Hydromorphone Bolus Protocol Versus the '1+1' Hydromorphone Titration Protocol in Treatment of Acute, Severe Pain in the First Hour of Emergency Department Presentation," Ann. Emerg. Med., May 20, 2013 (corrected proof).

Hayek, et al., "Analysis of long term effectiveness of continuous intrathecal infusion of hydromorphone and bupivacaine in combination with PTM," Pain Practice, 2012, vol. 12, Supp. S1, pp. 172-173, No. PP641.

Lee, et al., "Intrathecal hydromorphone added to hyperbaric bupivacaine for postoperative pain relief after knee arthroscopic surgery: a prospective, randomised controlled trial," Eur. J. Anaesthesiol., 2012, vol. 29, pp. 17-21.

Xia, et al., "Lack of Association Between Body Mass Index Clinical Response to 1 mg Intravenous Hydromorphone," Academic Emergency Medicine, May 2013, vol. 20, No. 5, Suppl. 1, pp. S226-S227, No. 565.

Butt, "Morphologic Changes Associated with Intrathecal Catheters for Direct Delivery to the Central Nervous System in Preclinical Studies," Toxicology Pathology, 2011, vol. 39, pp. 213-219 (published online Dec. 2010).

Knight, et al., "Implantable intrathecal pumps for chronic pain: highlights and updates," Croation Medical Journal, 2007, vol. 48(1), pp. 22-34.

Hildebrand, et al., "Stability, compatibility, and safety of intrathecal bupivacaine administered chronically via an implantable delivery system," Clinical Journal of Pain, 2001, vol. 17(3), pp. 239-244.

Murray, et al., "Hydromorphone," Journal of Pain and Symptom Management, 2005, vol. 29 (5 Suppl.), pp. S57-S66.

Sarhill, et al., "Hydromorphone: pharmacology and clinical applications in cancer patients," Supportive Care in Cancer, 2001, vol. 9, No. 2, pp. 84-96.

Quigley, "Hydromorphone for acute and chronic pain," Cochrane Database of Systematic Reviews, 2002, Issue 1, Art. No. CD003447.

Stearns, et al., "Intrathecal drug delivery for the management of cancer pain: a multidisciplinary consensus of best clinical practices," J. of Supportive Oncology, 2005, vol. 3(6), pp. 399-408.

"Intrathecal Drug Delivery for the Management of Pain and Spasticity in Adults, Recommendations for Best Clinical Practice," British Pain Society, Aug. 2008.

Newsome, et al., "Intrathecal analgesia for refractory cancer pain," Current Pain and Headache Reports, 2008, vol. 12(4), pp. 249-256.

Bennett, et al., "Intrathecal administration of an NMDA or a non-NMDA receptor antagonist reduces mechanical but not thermal allodynia in a rodent model of chronic central pain after spinal cord injury," Brain Research, 2000, vol. 859(1), pp. 72-82.

Chang, et al., "Safety and efficacy of hydromorphone as an analgesic alternative to morphine in acute pain: a randomized clinical trial," Annals of Emergency Medicine, 2006, vol. 48(2), pp. 164-172.

Coombs, et al., "Continuous intrathecal hydromorphone and clonidine for intractable cancer pain," Journal of Neurosurgery, 1986, vol. 64(6), pp. 890-894.

Kedlaya, et al., "Epidural and intrathecal analgesia for cancer pain," Best Practice and Research Clinical Anaesthesiology, 2002, vol. 16(4), pp. 651-665.

Smith, et al., "Intrathecal drug delivery," Pain Physician, 2008, vol. 11 (2 Suppl), pp. S89-S104.

Turner, et al., "Programmable intrathecal opioid delivery systems for chronic noncancer pain: a systematic review of effectiveness and complications," Clinical Journal of Pain, 2007, vol. 23(2), pp. 180-195.

Raffaeli, et al., "Intraspinal therapy for the treatment of chronic pain: a review of the literature between 1990 and 2005 and suggested protocol for its rational and safe use," Neuromodulation, 2006, vol. 9(4), pp. 290-308.

Saulino, "Successful reduction of neuropathic pain associated with spinal cord injury via of a combination of intrathecal hydromorphone and ziconotide: a case report," Spinal Cord, 2007, vol. 45(11), pp. 749-752.

Chiarella et al., "A Comparison of Intrathecal Hydromorphone with Morphine for Post-Operative Analgesia and Side Effects in Total Joint Arthroplasty," Anesthesiology and Pain Medicine, University of Alberta Hospital, Edmonton, Alberta, Canada, 2002.

Tobias, "A review of intrathecal and epidural analgesia after spinal surgery in children," Anesthesia and Analgesia, 2004, vol. 98(4), pp. 956-965.

McMillan, et al., "Catheter-associated masses in patients receiving intrathecal analgesic therapy," Anesthesia and Analgesia, 2003, vol. 96(1), pp. 186-190.

Coffey, et al., "Inflammatory mass lesions associated with intrathecal drug infusion catheters: report and observations on 41 patients," Neurosurgery, 2002, vol. 50 (1), pp. 78-86.

Trissel et al., "Physical and Chemical Stability of Hydromorphone Hydrochloride 1.5 and 80 mg/ml packaged in plastic syringes" Intl Journal of Pharma. Compounding; Jan. 2002; pp. 74-76.

Anonymous: "USP NF, The official compendia of standards", 2002, US Pharmacopeial Convention; p. 1579.

Williams et al., "Formulating Poorly Water Soluble Drugs", 2012, Springer, vol. 3; p. 230.

Gennaro, "Remington: the science and practice of pharmacy", 2000, Lippincott Williams & Wilkins, pp. 770-771; pp. 815-817.

* cited by examiner

STABILITY OF HYDROMORPHONE HYDROCHLORIDE SOLUTIONS

This application claims the benefit of priority of U.S. provisional application No. 61/607,774, filed Mar. 7, 2012, the disclosure of which is hereby incorporated by reference as if written herein in its entirety.

The present invention relates generally to a sterile hydromorphone hydrochloride solution that is substantially free of buffer.

Hydromorphone hydrochloride (sold as Dilaudid, Laudicon, Hydromorphan) is a narcotic analgesic, and one of its principle uses is the relief of pain. It is a semi-synthetic μ-opioid agonist. There is no intrinsic limit to the analgesic effect of hydromorphone hydrochloride; like morphine, adequate doses will relieve even the most severe pain. Hydromorphone is the generic (USAN) name (USP Dictionary of USAN and International Drug Names 2003) for 4,5-α-epoxy-3-hydroxy-17-methyl morphinan-6-one, a derivative of morphine. Its structural formula is:

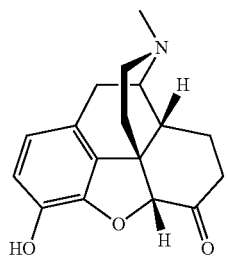

Presently, intrathecal hydromorphone hydrochloride is commercially available for injection in 10 mg/ml solutions in a preservative-free formula containing 0.2% sodium citrate and 0.2% of a citric acid solution.

Hydromorphone is used in medicine as an alternative to morphine and diacetylmorphine for analgesia and as a second- or third-line narcotic antitussive (cough suppressant) for cases of dry, painful, paroxysmal coughing resulting from continuing bronchial irritation after influenza and other ailments, inhalation of fungus and other causes, and is generally regarded to be the strongest of the latter class of drugs, and was developed shortly after another powerful antitussive, heroin, was removed from clinical use for this purpose in most of the world and in many countries banned outright.

The hydrogenation of morphine resulting in the formation of hydromorphone results in a drug with higher lipid solubility and ability to cross the blood-brain barrier and therefore more rapid and complete central nervous system penetration, with the result that hydromorphone is somewhat faster-acting and about eight times stronger than morphine and about three times stronger than heroin on a milligram basis. The effective morphine to hydromorphone conversion ratio can vary from patient to patient by a significant amount with relative levels of some liver enzymes being the main cause; the normal human range appears to be from 8:1 to a little under 4:1. It is not uncommon, for example, for the 8-mg tablet to have an effect similar to 30 mg of morphine sulfate or a similar morphine preparation.

The currently available hydromorphone hydrochloride solutions all contain buffer. The buffer is often added to a composition to regulate the pH and/or aid in the stability of the compound in solution. The addition of buffer can lead to potential complications such as toxicity, side effects and allergic responses. Further, the use of less or no buffer would decrease the costs of producing the pharmaceutical composition. Accordingly, there is a need for a hydromorphone hydrochloride solution that does not contain buffer. Surprisingly, it has been found that hydromorphone hydrochloride in water does not require buffering agents to maintain it stability over time.

Recently, there has been increasing interest in the regulation of the cerebrospinal fluid (CSF) pH. Part of this interest stems from the fact that the extracellular fluid (ECF) pH in the brain serves as an important regulator of pulmonary ventilation and a major determinant of cerebral blood flow. Furthermore, since the CSF pH has been shown to be subject to a considerable degree of homeostatic control in a variety of conditions which change the acid-base status of blood, many attempts have been made to unravel the physiological mechanisms which are responsible for this control. Finally, since the acid-base metabolism of the cerebral compartments (including the ECF) may influence cerebral function to a significant degree, the CSF pH and the mechanisms which regulate it have become of concern to neurologists and neurosurgeons. CSF normally has a pH near 7.3. Since intrathecal delivery of hydromorphone hydrochloride is direct injection into the CSF, and it is desirable to keep the pH of the resulting CSF—hydromorphone solution mixture as close to 7.3 as possible, injection of a hydromorphone hydrochloride formulation with a pH near 7.3 is appealing. Indeed, the pH of the formulation without buffer is closer to the natural physiological pH of CSF than the formulation containing buffer (5.0 vs 4.1).

While there are no absolute FDA standards for sterilization processes, pharmaceutical solutions are most commonly sterilized using a heating regimen at 121.1° C. with an $F_o$ of about 30 minutes. While this may be an effective method for thermally stable compounds, this practice is counterproductive for some heat-labile active pharmaceutical ingredients (API's). In these cases, the resulting solution may be sterile, but it is often plagued with an unacceptable increase in degradation products brought on by the excessive use of heat in the sterilization process. Furthermore, compositions containing heat-labile API's are often not terminally sterilized to avoid this degradation. Therefore, it is desirable to find and implement a sterilization method that utilizes less harsh conditions in order to prevent this thermal degradation from taking place, while continuing to meet sterility standards.

Indeed, during the terminal sterilization process, heat-labile hydromorphone undergoes transformations to undesirable side products such as hydromorphone N-oxide (HNO), 6-β-tetrahydrooripavine (THO), dihydromorphone (DHM), and pseudo-hydromorphone (PHM). This obviously reduces the amount of hydromorphone in solution, and thus the overall efficacy of the solution. Additionally, this degradation product may have undesirable side effects, including toxicity. The amount of side products found in commercially available hydromorphone solutions is shown in the table below.

| Hydromorphone Hydrochloride (Commercial) 10 mg/mL | | | |
| --- | --- | --- | --- |
| % HNO | % THO | % DHM | % PHM |
| <0.05 | <0.05 | <0.05 | 0.5 |

An alternative to terminal sterilization is aseptic processing, which is the process by which a sterile (aseptic) product is packaged in a sterile container in a way which maintains sterility. This avoids the harsh conditions of terminal sterilization without sacrificing sterility of the resulting solution. It was hypothesized that aseptic processing may lead to a solution with fewer degradation products, as the hydromorphone would not be subjected to the rigors of the terminal sterilization process.

Therefore, there is a clinical need for aqueous solutions of hydromorphone having fewer degradation products, preferably for concentrated solutions that are also stable in a variety of storage conditions for extended periods of time. Due to the heat-lability of the hydromorphone product, aseptic processing is herein disclosed for the reduction of impurities in the hydromorphone solution.

Disclosed herein is a pharmaceutical composition comprising a sterile, intrathecal, aqueous hydromorphone hydrochloride solution, wherein said composition is substantially free of buffer.

In an embodiment, a solution of intrathecal hydromorphone hydrochloride contains less than 1.0% pseudo-hydromorphone.

According to a further aspect, a solution of intrathecal hydromorphone hydrochloride contains less than 0.1% pseudo-hydromorphone.

In an embodiment, a solution of intrathecal hydromorphone hydrochloride contains less than 0.2% hydromorphone N-oxide.

According to another aspect, a solution of intrathecal hydromorphone hydrochloride is substantially free of hydromorphone N-oxide.

According to another aspect, a solution of intrathecal hydromorphone hydrochloride is substantially free of dihydromorphone.

According to another aspect, a solution of intrathecal hydromorphone hydrochloride is substantially free of 6-β-tetrahydrooripavine.

According to one embodiment, the solution described herein is not terminally sterilized.

According to another aspect, the solution described herein is free of particulates.

According to yet another aspect, the solution described herein is stable at 25° C. and 60% relative humidity for at least 1 month.

According to yet another aspect, the solution described herein is stable at 30° C. and 65% relative humidity for at least 1 month.

According to a further aspect, the solution described herein is stable at 40° C. and 75% relative humidity for at least 1 month.

According to yet another aspect, the solution described herein is stable at 25° C. and 60% relative humidity for at least 3 months.

According to yet another aspect, the solution described herein is stable at 30° C. and 65% relative humidity for at least 3 months.

According to a further aspect, the solution described herein is stable at 40° C. and 75% relative humidity for at least 3 months.

According to yet another aspect, the solution described herein is stable at 25° C. and 60% relative humidity for at least 6 months.

According to yet another aspect, the solution described herein is stable at 30° C. and 65% relative humidity for at least 6 months.

According to a further aspect, the solution described herein is stable at 40° C. and 75% relative humidity for at least 6 months.

According to yet another aspect, the solution described herein is stable at 25° C. and 60% relative humidity for at least 1 year.

According to yet another aspect, the solution described herein is stable at 30° C. and 65% relative humidity for at least 1 year.

According to a further aspect, the solution described herein is stable at 40° C. and 75% relative humidity for at least 1 year.

According to yet another aspect, the solution described herein is stable at 25° C. and 60% relative humidity for at least 2 years.

According to yet another aspect, the solution described herein is stable at 30° C. and 65% relative humidity for at least 2 years.

According to a further aspect, the solution described herein is stable at 40° C. and 75% relative humidity for at least 2 years.

According to another aspect, the solution described herein is suitable for intrathecal delivery.

Disclosed herein is a pharmaceutical composition consisting of a sterile, aqueous solution of hydromorphone hydrochloride.

In an embodiment, the concentration of the hydromorphone hydrochloride solution is 10.0 mg/mL.

In an embodiment, the concentration of the hydromorphone hydrochloride solution is 2.0 mg/mL.

Disclosed herein is a method of treating pain by administration of a sterile aqueous solution of hydromorphone hydrochloride, wherein said composition is substantially free of buffer.

As used herein, the terms below have the meanings indicated.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "sterile," as used herein, means free from all live bacteria or other microorganisms and their spores.

The term "particulate," as used herein, is meant to describe mobile undissolved particles, other than gas bubbles, unintentionally present in the drug solution.

The term "intrathecal," as used herein, means introduced into or occurring in the space under the arachnoid membrane which covers the brain and spinal cord. Intrathecal drug delivery is designed to manage chronic pain and/or spasticity, such as intractable cancer pain, by delivering pain medication directly to the intrathecal space. Intrathecal drug delivery uses an implantable infusion system to deliver pain medication directly to the intrathecal space via a surgically implanted infusion pump and catheter.

The term "stable" as used herein in reference to claimed compositions means retaining substantially the same properties and characteristics throughout its period of storage and use that it possessed at the time of its manufacture, such that the composition provides substantially the same therapeutic benefit to the patient over the period of time that the composition is stored and delivered, such as for 1 month, 3 months, 6 months, 1 year, or 2 years. The compositions disclosed herein are stable if they contain within 3% of the amount of hydromorphone hydrochloride as claimed on the label (% LC) after 12 weeks, as determined by HPLC assay.

Certain embodiments disclosed herein may be illustrated by the following non-limiting examples.

EXAMPLE 1

Preparation of 10.0 mg/mL Hydromorphone Hydrochloride Solution with 0.2% Citrate Buffer To 1 L of water for injection (WFI) is added 40.4 g citrate buffer, and the mixture is stirred for 10±2 minutes. To the resulting solution is added 200.0 g hydromorphone hydrochloride and 2 L WFI. The mixture is then stirred for 45 minutes. The resulting solution is diluted to 20 L with WFI and stirred for at least an additional 10 minutes.

EXAMPLE 2

Preparation of 10.0 mg/mL Hydromorphone Hydrochloride Solution with 0.1% Citrate Buffer To 1 L of WFI is added 20.2 g citrate buffer, and the mixture is stirred for 10±2 minutes. To the resulting solution is added 200.0 g hydromorphone hydrochloride and 2 L WFI. The mixture is then stirred for 45 minutes. The resulting solution is diluted to 20 L with WFI and stirred for at least an additional 10 minutes.

EXAMPLE 3

Preparation of 10.0 mg/mL Hydromorphone Hydrochloride Solution with 0.05% Citrate Buffer To 1 L of WFI is added 10.1 g citrate buffer, and the mixture is stirred for 10±2 minutes. To the resulting solution is added 200.0 g hydromorphone hydrochloride and 2 L WFI. The mixture is then stirred for 45 minutes. The resulting solution is diluted to 20 L with WFI and stirred for at least an additional 10 minutes.

EXAMPLE 4

Preparation of 10.0 mg/mL Hydromorphone Hydrochloride Solution with 0.03% Citrate Buffer To 1 L of WFI is added 6.06 g citrate buffer, and the mixture is stirred for 10±2 minutes. To the resulting solution is added 200.0 g hydromorphone hydrochloride and 2 L WFI. The mixture is then stirred for 45 minutes. The resulting solution is diluted to 20 L with WFI and stirred for at least an additional 10 minutes.

EXAMPLE 5

Preparation of 10.0 mg/mL Hydromorphone Hydrochloride Solution with 0% Citrate Buffer To 3 L of WFI is added 200.0 g hydromorphone hydrochloride. The mixture is stirred for 45 minutes. The resulting solution is diluted to 20 L with WFI and stirred for at least an additional 10 minutes.

EXAMPLE 6

Impurity Profile of Hydromorphone Hydrochloride Solutions with Varying Amounts of Buffer The impurity profile of Examples 1-5, showing the amount of each impurity, as well as the percent of the label claim (% LC) of the API, as determined by HPLC assay.

| Buffer-containing Solutions | | | | | | | |
|---|---|---|---|---|---|---|---|
| % Buffer | pH | % L.C. | % HMN | % DHM | % THO | %0.56 RRT | % Pseudo-HM |
| 0 | 5.0 | 99.0 | <0.05 | <0.05 | <0.05 | <0.05 | <0.05 |
| 0.03 | 4.2 | 100.4 | <0.05 | <0.05 | <0.05 | <0.05 | <0.05 |
| 0.05 | 4.1 | 101.1 | <0.05 | <0.05 | <0.05 | <0.05 | <0.05 |
| 0.1 | 4.1 | 100.7 | <0.05 | <0.05 | <0.05 | <0.05 | 0.05 |
| 0.2 | 4.1 | 100.1 | <0.05 | <0.05 | <0.05 | <0.05 | <0.05 |

EXAMPLE 7

Impurity Profile of Hydromorphone Hydrochloride Solution with 0% Buffer Over Time The impurity profile of Example 5 over time, showing the amount of each impurity, as well as the percent of the label claim (% LC) of the API, as determined by HPLC assay.

| Time (Days) | pH | % L.C. | % HMN | % DHM | % THO | % Pseudo-HM |
|---|---|---|---|---|---|---|
| 0 | 5.0 | 99.0 | <0.05 | <0.05 | <0.05 | <0.05 |
| 3 | — | 97.7 | <0.05 | <0.05 | <0.05 | <0.05 |
| 7 | — | 99.7 | <0.05 | <0.05 | <0.05 | <0.05 |
| 14 | 4.6 | 102.4 | <0.05 | <0.05 | <0.05 | 0.06 |
| 28 | 4.6 | 99.3 | <0.05 | <0.05 | <0.05 | 0.07 |
| 56 | 4.6 | 99.0 | <0.05 | <0.05 | <0.05 | 0.07 |
| 84 | 4.5 | 100.5 | <0.05 | <0.05 | <0.05 | 0.09 |

The data shows that compositions containing buffer have the same levels of impurities as the composition without buffer. This indicates that the buffer is not an essential part of the composition from an impurity standpoint. Further, additional data shows that the buffer-free composition maintains its low levels of impurities over time, indicating that buffer is not essential to the long-term stability of the composition.

The formulation without buffer has a small pH change (only 0.5 pH units) over the time period tested. This indicates that the buffer is not necessary to keep the pH stable over time. This pH data, coupled with the impurity data, shows that the small change in pH that is observed does not have a detrimental effect on the purity of the formulation. Further, the absence of the buffer gives the formulation a pH closer to the patient's natural physiological pH of the cerebrospinal fluid than the formulation containing the buffer (5.0 vs. 4.1).

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition consisting of a sterile aqueous solution of hydromorphone hydrochloride, wherein said composition is stable at 25° C. and 60% relative humidity for at least 3 months.

2. The composition as recited in claim 1, wherein said composition is suitable for intrathecal delivery.

3. A pharmaceutical composition consisting of a sterile aqueous solution of hydromorphone hydrochloride, wherein said composition is stable at 30° C. and 65% relative humidity for at least 3 months.

4. A pharmaceutical composition consisting of a sterile aqueous solution of hydromorphone hydrochloride, wherein said composition is stable at 40° C. and 75% relative humidity for at least 3 months.

5. The composition as recited in claim 1, wherein said composition is sterilized via aseptic processing.

6. The composition as recited in claim 1, having a liquid drug formulation wherein the concentration of hydromorphone hydrochloride is about 10.0 mg/mL.

7. The composition as recited in claim 1, having a liquid drug formulation wherein the concentration of hydromorphone hydrochloride is about 2.0 mg/mL.

8. A method of treating pain, the method comprising: intrathecal delivery of the pharmaceutical composition of claim 1 to a patient.

* * * * *